(12) United States Patent
Fujieda (10) Patent No.: US 7,123,751 B1
(45) Date of Patent: Oct. 17, 2006

(54) OPHTHALMIC APPARATUS, OPHTHALMIC SYSTEM AND METHOD FOR MANAGING OPHTHALMIC DATA

(75) Inventor: Masanao Fujieda, Toyohashi (JP)

(73) Assignee: Nidek Co., Ltd., Aichi (JP)

( * ) Notice: Subject to any disclaimer, the term of this patent is extended or adjusted under 35 U.S.C. 154(b) by 276 days.

(21) Appl. No.: 09/584,977

(22) Filed: Jun. 2, 2000

(30) Foreign Application Priority Data

Jun. 3, 1999 (JP) ............ HEI 11-156822

(51) Int. Cl.
*G06K 9/00* (2006.01)

(52) U.S. Cl. ............ 382/115; 340/5.53; 340/5.83; 382/117; 396/18

(58) Field of Classification Search ............ 356/71; 340/5.53, 5.83; 902/3, 6; 396/18; 351/206; 382/115, 116, 117, 118, 124; 606/4, 5, 6, 606/107, 166
See application file for complete search history.

(56) References Cited

U.S. PATENT DOCUMENTS

| | | | | |
|---|---|---|---|---|
| 4,461,028 A | * | 7/1984 | Okubo | 382/115 |
| 4,641,349 A | | 2/1987 | Flom et al. | |
| 4,669,466 A | * | 6/1987 | L'Esperance | 606/3 |
| 5,071,168 A | * | 12/1991 | Shamos | 283/117 |
| 5,157,603 A | * | 10/1992 | Scheller et al. | 606/4 |
| 5,500,697 A | | 3/1996 | Fujieda | |
| 5,827,264 A | | 10/1998 | Hohla | |
| 5,891,132 A | * | 4/1999 | Hohla | 606/5 |
| 5,906,608 A | | 5/1999 | Sumiya et al. | |
| 5,907,388 A | | 5/1999 | Fujieda | |
| 5,926,555 A | * | 7/1999 | Ort et al. | 382/124 |
| 6,033,075 A | | 3/2000 | Fujieda et al. | |
| 6,173,068 B1 | * | 1/2001 | Prokoski | 382/115 |
| 6,296,634 B1 | * | 10/2001 | McMillen et al. | 606/10 |

FOREIGN PATENT DOCUMENTS

| | | |
|---|---|---|
| EP | 0 765 648 A2 | 4/1997 |
| JP | 9-234186 | 9/1997 |

* cited by examiner

*Primary Examiner*—Bhavesh M. Mehta
*Assistant Examiner*—Sath V. Perungavoor
(74) *Attorney, Agent, or Firm*—Finnegan, Henderson, Farabow, Garrett & Dunner, LLP (57) ABSTRACT

An ophthalmic apparatus comprising an optometry device for examining or measuring a patient's eye to obtain measurement data on the eye, a photographing device for photographing the eye, an identification code generating device for extracting a characteristic, which is inherently unique to the eye, from an image of the eye photographed by the photographing device and generating an identification code for the use of eye identification based on the extracted characteristic, and an output device for outputting obtained measurement data in association with the generated identification code.

3 Claims, 9 Drawing Sheets

OPHTHALMIC APPARATUS, OPHTHALMIC SYSTEM AND METHOD FOR MANAGING OPHTHALMIC DATA

BACKGROUND OF THE INVENTION

1. Field of the Invention

The present invention relates to ophthalmic apparatus, ophthalmic systems and methods for managing ophthalmic data.

2. Description of Related Art

Referring to measurement data obtained by ophthalmic apparatus, for example a refractometer, a corneal topography apparatus (a corneal shape measuring apparatus), a noncontact tonometer, a fundus camera, an analyzer for analyzing anterior eye segment or fundus and the like, such measurement data (data on characteristics of eyes) are normally assigned identification codes in order to manage the data using the identification codes. Typically, the identification codes are names or telephone numbers of patients, identification numbers or the like. However, in the case where the measurement data are inputted to, and used by another ophthalmic apparatus, management of the data using the above-mentioned identification codes is not regarded to be sufficient.

One example is the case of a corneal surgery apparatus, which corrects a refractive error of a patient's eye by ablating a cornea of the eye with excimer laser beam to alter the corneal curvature. In this case, measurement data on the patient's eye such as preoperative corneal topography data are inputted the apparatus prior to the surgery. The surgery is carried out based on a correction amount (an amount of the cornea to be ablated) calculated from the inputted measurement data. However, there is a possibility that the patient's eye to be operated and the measurement data do not correspond to each other due to an input error of the identification code assigned to the measurement data or other errors. Alternatively, there is a possibility that the measurement data for right eye or left eye on the same patient are inadvertently mistaken for another. In these cases, an intended outcome of the surgery can not be achieved.

Further, in the case where a large number of measurement data are managed by a data base computer, the above-mentioned data management using identification codes alone is insufficient to ensure matching of the data with the identification codes: if there is an input error of an identification code, the data and the identification code do not match. In addition, in the case of data management by a computer, it is desired to manage measurement data separately on each patient's eye (patient) with accuracy and also to save storage capacity as much as possible.

SUMMARY OF THE INVENTION

The present invention has been made in view of the above circumstances and has an object to overcome the above problems and to provide an ophthalmic apparatus and an ophthalmic system capable of managing measurement data in association with each patient's eye (patient) using strict (highly reliable) identification codes.

It is another object of the present invention to provide an ophthalmic apparatus and an ophthalmic system capable of avoiding inconsistency between a patient's eye to be operated and measurement data obtained by another ophthalmic apparatus.

It is yet another object of the present invention to provide an ophthalmic apparatus, an ophthalmic system and a method for managing ophthalmic data capable of managing measurement data obtained by a plurality of apparatus while saving storage capacity.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an ophthalmic apparatus comprises optometry means for examining or measuring a patient's eye to obtain measurement data on the eye, photographing means for photographing the eye, identification code generating means for extracting a characteristic, which is inherently unique to the eye, from an image of the eye photographed by the photographing means and generating an identification code for the use of eye identification based on the extracted characteristic, and output means for outputting obtained measurement data in association with the generated identification code.

In another aspect of the present invention, an ophthalmic apparatus comprises photographing means for photographing a patient's eye, identification code generating means for extracting a characteristic, which is inherently unique to the eye, from an image of the eye photographed by the photographing means and generating a first identification code for the use of eye identification based on the extracted characteristic, input means for inputting measurement data on the eye obtained by a different ophthalmic apparatus in association with a second identification code, which is generated in the same form as the first identification code, comparison means for comparing the first identification code and the second identification code to see if they match, and informing means for informing a result of the comparison by the comparison means.

Further, in another aspect of the present invention, a method for managing ophthalmic data comprising steps of inputting measurement data on a patient's eye, to which an identification code is assigned, the identification code being generated based on a characteristic, which is inherently unique to the eye, comparing the identification codes assigned to the inputted measurement data to see if they match in the case where a plurality of measurement data are inputted, and storing the measurement data in association with at least one identification code that is obtained by integrating the identification codes if it is judged that the identification codes match.

Further, in another aspect of the present invention, an ophthalmic apparatus comprises input means for inputting measurement data on a patient's eye, to which an identification code is assigned, the identification code being generated based on a characteristic, which is inherently unique to the eye, comparison means for comparing the identification codes assigned to the inputted measurement data to see if they match in the case where a plurality of measurement data are inputted, and storage means for storing the measurement data in association with at least one identification code that is obtained by integrating the identification codes if it is judged that the identification codes match.

Further, in another aspect of the present invention, an ophthalmic system comprises an ophthalmic apparatus and a data management apparatus. The ophthalmic apparatus includes optometry means for examining or measuring a patient's eye to obtain measurement data on the eye, photographing means for photographing the eye, identification code generating means for extracting a characteristic, which is inherently unique to the eye, from an image of the eye photographed by the photographing means and generating an identification code for the use of eye identification based on the extracted characteristic, and output means for outputting obtained measurement data in association with the generated identification code. The data management apparatus includes input means for inputting the outputted measurement data in association with the identification code, comparison means for comparing the identification codes assigned to the inputted measurement data to see if they match in the case where a plurality of measurement data are inputted, and storage means for storing the measurement data in association with at least one identification code that is obtained by integrating the identification codes if it is judged that the identification codes match.

Further, in another aspect of the present invention, an ophthalmic system comprises an ophthalmic apparatus and a surgery apparatus. The ophthalmic apparatus includes optometry means for examining or measuring a patient's eye to obtain measurement data on the eye, first photographing means for photographing the eye, first identification code generating means for extracting a characteristic, which is inherently unique to the eye, from an image of the eye photographed by the first photographing means and generating a first identification code for the use of eye identification based on the extracted characteristic, and output means for outputting obtained measurement data in association with the generated first identification code. The surgery apparatus includes surgery means for performing surgery on the eye, second photographing means for photographing the eye, second identification code generating means for extracting the characteristic, which is inherently unique to the eye, from an image of the eye photographed by the second photographing means and generating a second identification code for the use of eye identification in the same form as the first identification code based on the extracted characteristic, input means for inputting the outputted measurement data in association with the first identification code, comparison means for comparing the first identification code and the second identification code to see if they match, and informing means for informing a result of the comparison by the comparison means.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
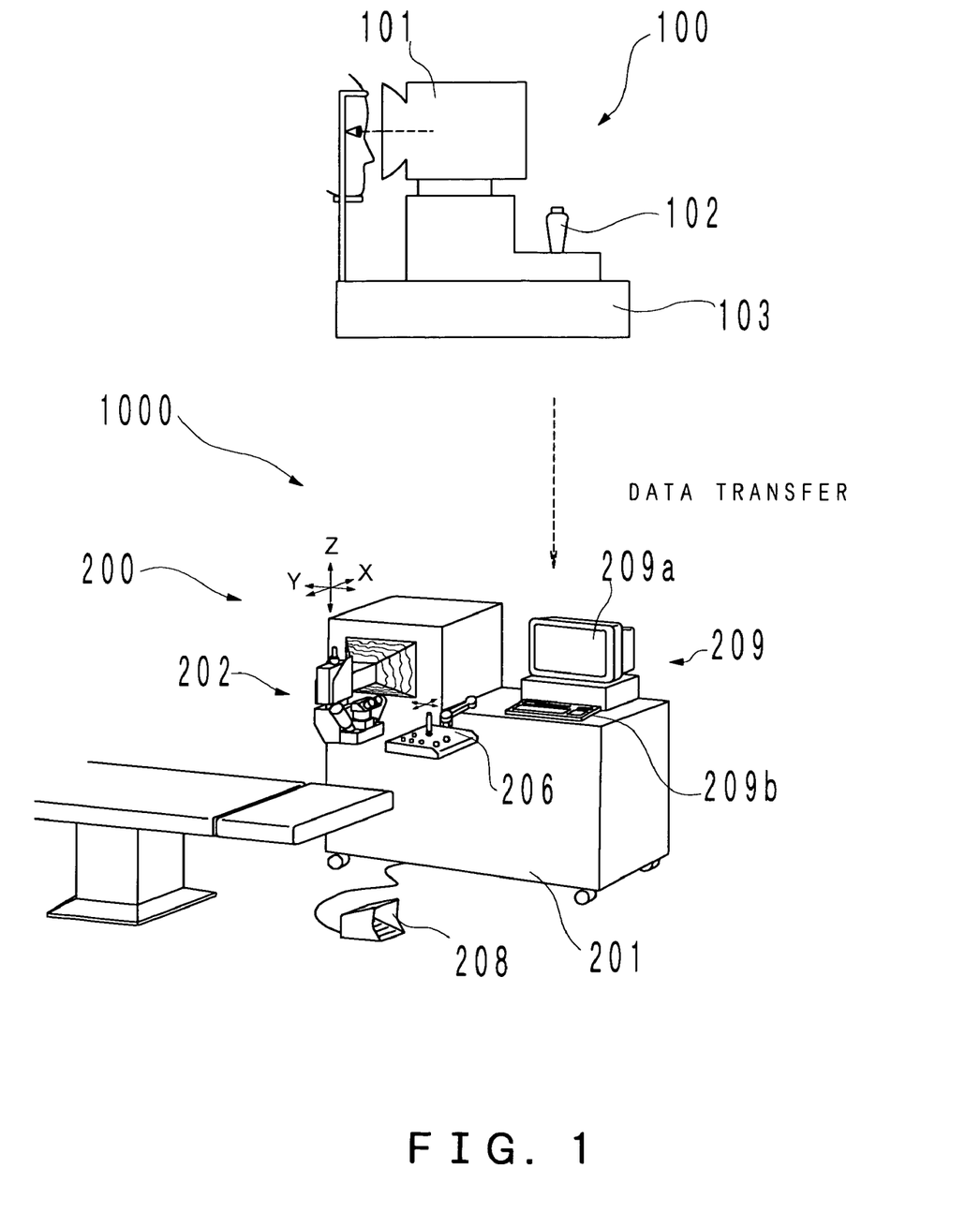
FIG. 1 is a view showing an external representation of an ophthalmic system consistent with a preferred embodiment of the present invention.

A detailed description of one preferred embodiment of an ophthalmic apparatus, an ophthalmic system and a method for managing ophthalmic data embodying the present invention will now be given referring to the accompanying drawings. FIG. 1 is a view showing an external representation of an ophthalmic system 1000 of this preferred embodiment. Reference numeral 100 is a corneal topography apparatus which is one component of the system 1000. 200, which is also one component of the system 1000, is a corneal surgery apparatus for ablating a cornea with excimer laser beam having a wavelength of 193 nm. In this embodiment, description is given to an example in which measurement data (data on eye characteristics, namely corneal topography data in this case) obtained by the corneal topography apparatus 100 are inputted to, and used by the corneal surgery apparatus 200. First, description is given to configuration of the corneal topography apparatus 100 and the corneal surgery apparatus 200 separately.

Corneal Topography Apparatus

Figure 2:
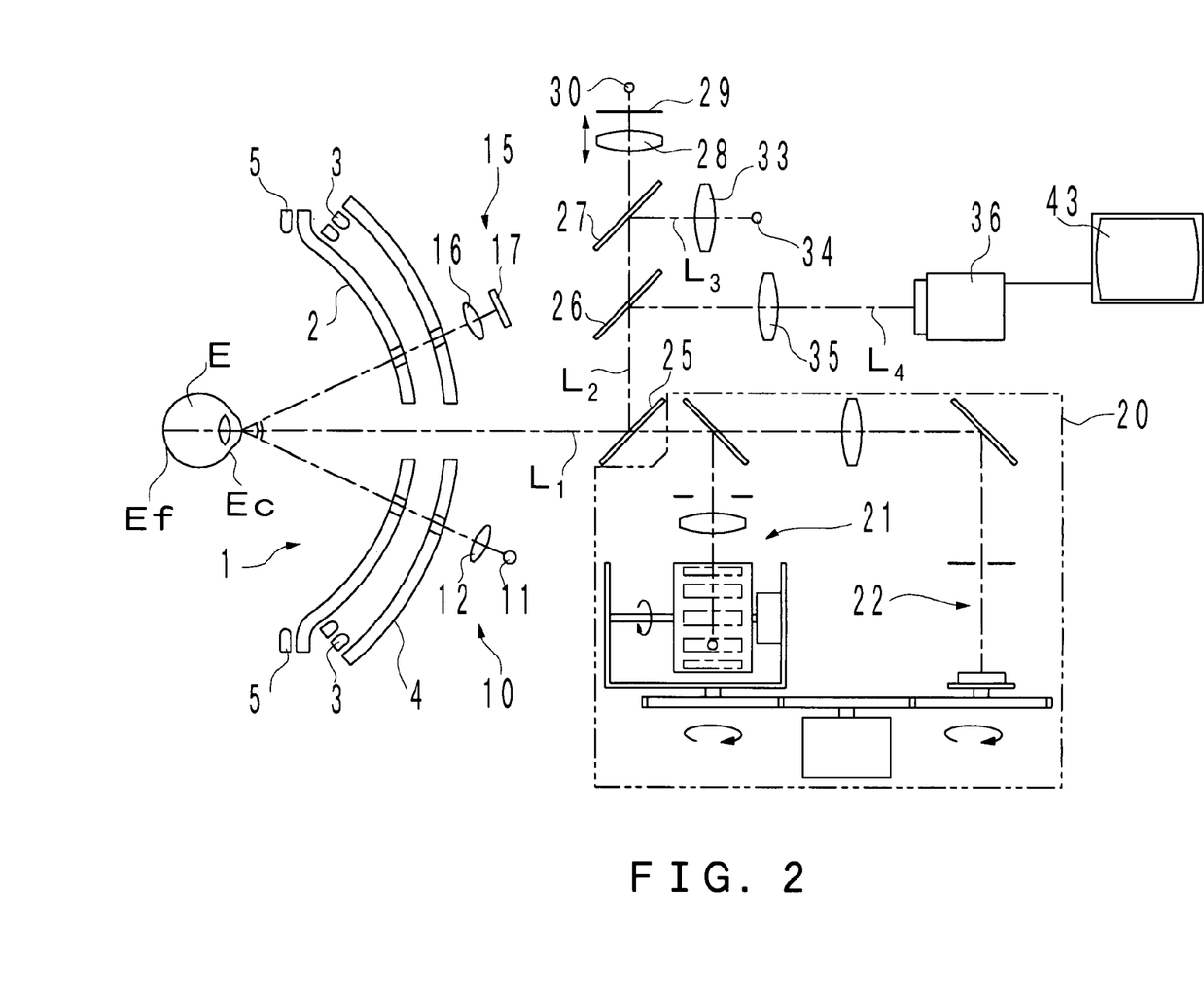
FIG. 2 is a view showing a schematic configuration of an optical system included in a corneal topography apparatus.

FIG. 2 is a view showing a schematic configuration of an optical system included in the corneal topography apparatus 100 for measuring and analyzing a corneal shape, which also has a function of eye refractive power measurement.

Reference numeral 1 denotes a target projecting optical system for measuring a corneal shape. 2 is a placido plate generally of a dome-shape having an opening at the center thereof, in which a ring pattern is formed with a number of concentric circles of light transmitting portions and light shielding portions with an optical axis L1 as the center. 3 are illumination light sources such as LEDs or the like. Light emitted from the light sources 3 is reflected by a reflecting plate 4 and illuminates the placido plate 2 uniformly from behind so that an image of the ring pattern is formed on a cornea Ec of a patient's eye E. On an outer circumference of the placido plate 2, anterior eye segment illumination lights 5 which emit near infrared light are disposed.

Disposed behind the reflecting plate 4 are an alignment target projecting optical system 10 for working distance and an alignment target detecting optical system 15 for working distance: the former comprises a light source 11 which emits near infrared light and a lens 12, and the latter comprises a lens 16 and a position detecting element 17. Light emitted form the light source 11 is made generally parallel light by the lens 12 and enters into the cornea Ec obliquely through each opening provided in the reflecting plate 4 and the placido plate 2 thereby forming a target image on the cornea Ec. The light of the target image that has formed on the cornea Ec passes through each opening provided in the reflecting plate 4 and the placido plate 2 and enters into the position detecting element 17 via the lens 16. Based on an incident position of the light of the target image on the position detecting element 17, an alignment condition of the eye E with the apparatus in a working distance direction is detected.

An eye refractive power measurement optical system 20 is provided in a rear direction along the optical axis L1. The eye refractive power measurement optical system 20 can be of any conventional type. In this embodiment, one disclosed in U.S. Pat. No. 5,907,388 (Japanese Unexamined Patent Publication No. HEI 10(1998)-108837) by the present applicant is used. This eye refractive power measurement optical system 20 comprises a slit light projecting optical system 21 for scanning a fundus Ef of the eye E with a slit light bundle, and a slit light detecting optical system 22 which is provided with pairs of photodetectors arranged symmetric with a measurement optical axis (and also, one pair of photodetectors is arranged along a meridian direction that is parallel to a longitudinal direction of the slit projected by the slit light bundle) at a generally conjugate position with the cornea Ec. By rotating the slit light bundle and the photodetectors about the optical axis in synchronism, refractive power, which varies along a meridian direction is obtained at a plurality of corneal portion based on output signals from each photodetector indicating the phase difference.

In addition, a beam splitter 25 is provided on the optical axis L1. Disposed on an optical axis L2, which is made coaxial with the optical axis L1 by the beam splitter 25 are half mirrors 26 and 27, a lens 28, a fixation target 29 and an illumination light source 30 which emits visible light. The fixation target 29 has a fixation point in the middle and an area surrounding the fixation point transmits visible light. The lens 28 is movable along the optical axis L2 so as to change visibility of the fixation target 28 on which the eye E is made fixate.

Disposed on an optical axis L3, which is made coaxial with the optical axis L2 by the half mirror 27 are a lens 33, a light source 34 which emits near infrared light. Light emitted from the light source 34 is made generally parallel light by the lens 33 and enters into the cornea Ec from the front, thereby forming a target image on the cornea Ec for alignment in right-and-left and up-and-down directions.

Disposed on an optical axis L4, which is made coaxial with the optical axis L2 by the half mirror 26 are a lens 35 and a CCD camera 36 serving as a photographic element. Picture signals outputted from the CCD camera 36 are inputted into a TV monitor 43. The CCD camera 36 is used for observing an anterior eye segment of the eye E as well as for photographing the image of the placido ring formed on the cornea Ec, detecting the image of the alignment target formed by the light emitted from the light source 34, and photographing an anterior eye segment for patient's eye identification, which will be described later.

Figure 3:
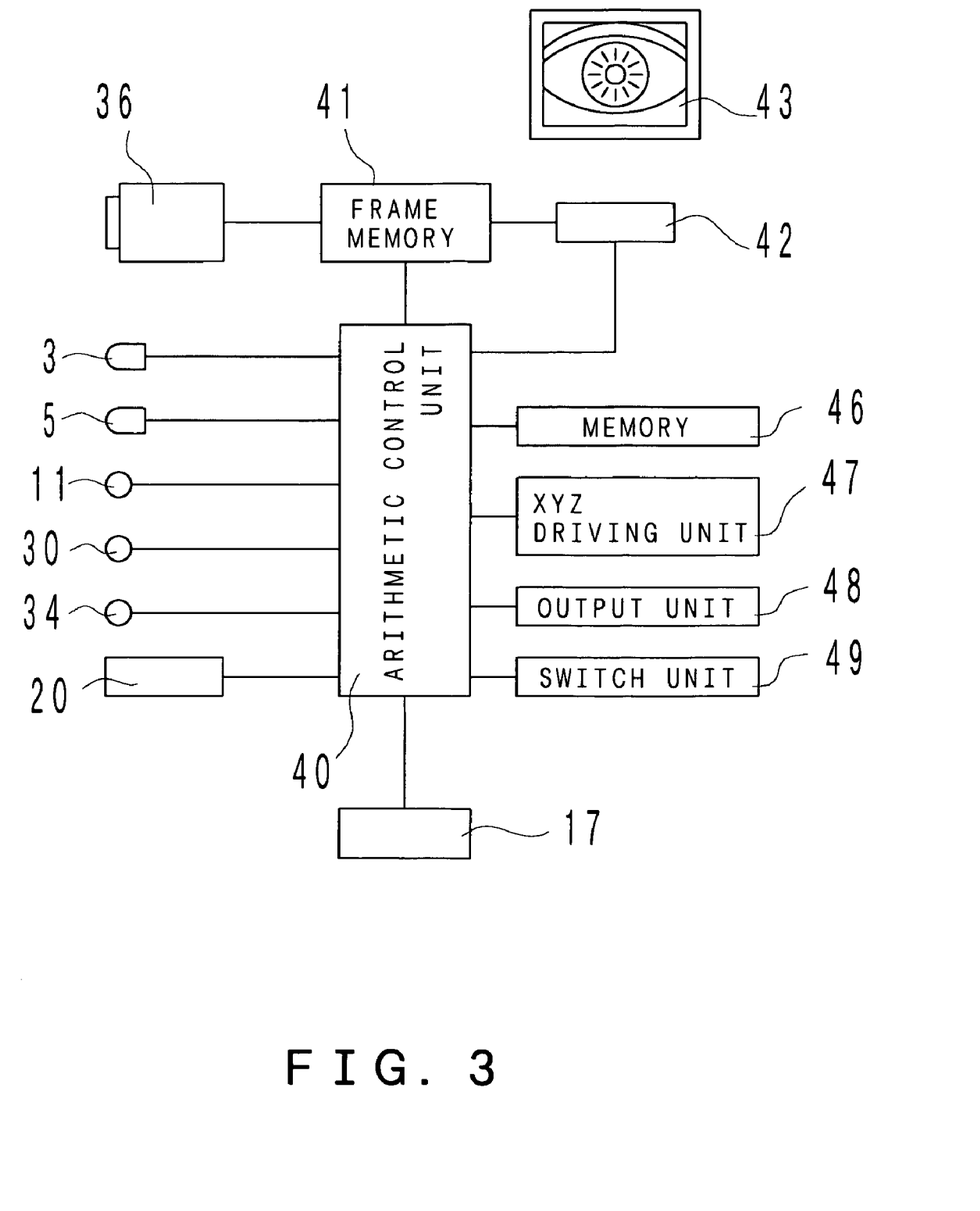
FIG. 3 is a block diagram showing an important part of a control system of the corneal topography apparatus.

FIG. 3 is a block diagram showing an important part of a control system of the corneal topography apparatus 100. Reference numeral 41 denotes a frame memory for capturing the image outputted from the CCD camera 36. 42 is an image change-over circuit, 43 is the color TV monitor, 46 is a memory for storing data. 47 is an XYZ driving unit comprising a mechanism for electrically driving a measurement unit 101, which contains the above optical system therein (see FIG. 1) in each directions of right-and-left (X), up-and-down (Y), and back-and-forth (Z) relative to the eye E. 40 is an arithmetic control unit for controlling each unit of the apparatus. Based on the image captured in the frame memory 41, the arithmetic control unit 40 judges alignment condition of the apparatus by detecting each alignment target image, analyzes corneal shape, and generates identification codes to identify the eye E by extracting characteristics of the iris pattern of the eye E.

Here, description is given to generation of identification codes of patients' eyes based on the iris patterns. In an iris of a human eye, there are formed various patterns with radially extending black lines, an outline of outer circumference and the like. The patterns differ from person to person, and more precisely, the patterns differ from the right eye to the left eye of the same individual. In other words, just like finger prints, the iris patterns have characteristics that are inherently unique to each living body, and thus are excellent to identify each individual and each eye of the same individual. Taking this advantage, identification codes to identify individual eyes are generated from photographed images of anterior eye segments in the following manner: first, an iris pattern is obtained by picking up the boundary between the pupil and the iris; then, coordinates representing the light and shade in the thus obtained iris pattern are extracted by performing optical scanning along a predetermined line; and finally, the identification codes are obtained by digitizing the coordinates. For the detail of identification using iris, see, for example, U.S. Pat. No. 4,641,349 (Japanese Examined Patent Publication No. HEI 5(1993)-84166) and the like.

Corneal Surgery Apparatus

Figure 4:
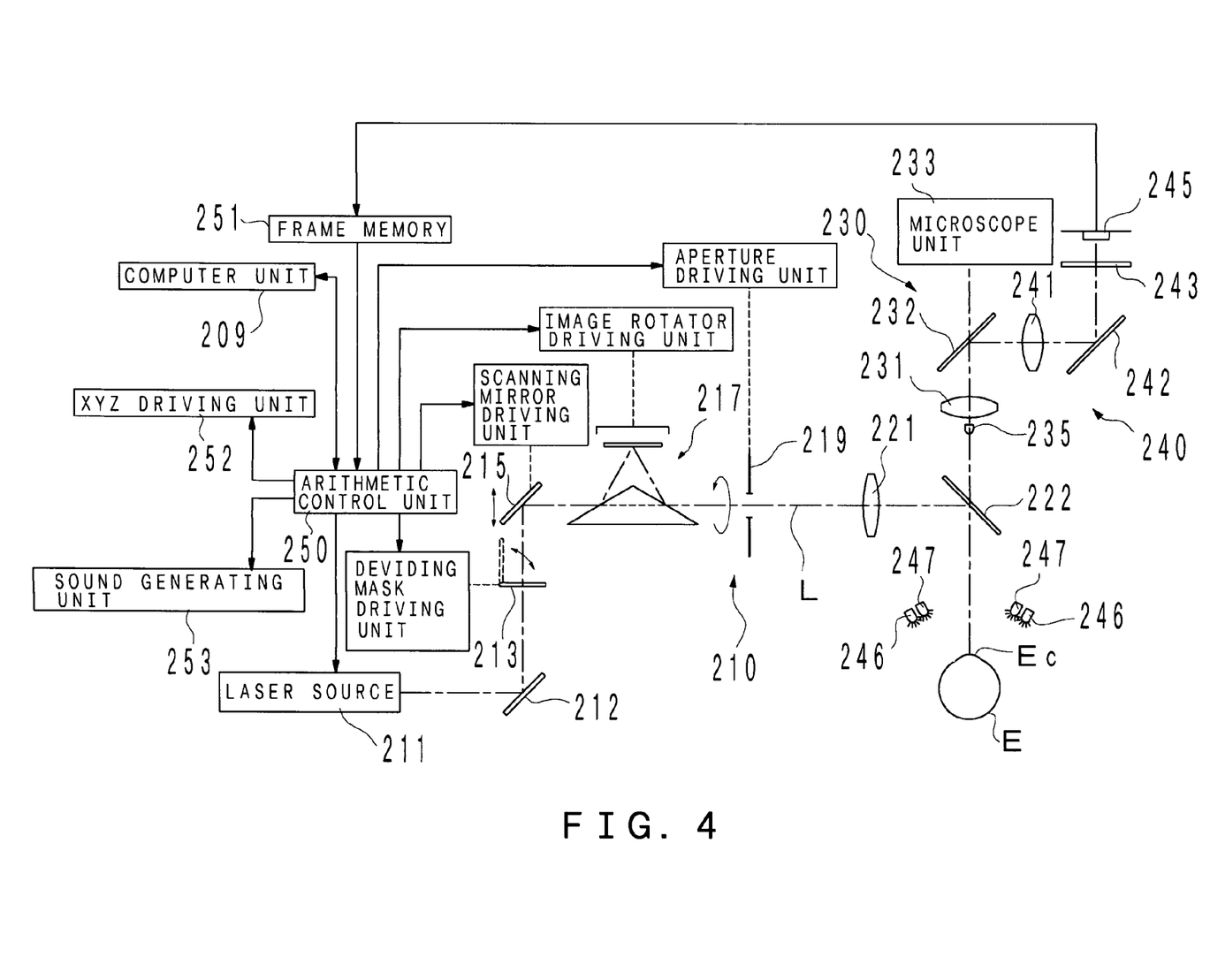
FIG. 4 is a schematic view showing an optical system and a control system of a corneal surgery apparatus.

Description is now given to configuration of the corneal surgery apparatus 200 referring to FIGS. 1 and 4. FIG. 4 is a view showing a schematic configuration of an optical system and a control system of the corneal surgery apparatus 200.

In FIG. 1, reference numeral 201 is a main body of the apparatus that contains an excimer laser source and the like therein. Excimer laser beam (hereinafter referred to simply as "laser beam") emitted from the main body 201 is directed to an arm unit 202. The arm unit 202 comprises part of a laser irradiation optical system 210, an observation optical system 230 and an eye-ball position detecting optical system 240 shown in FIG. 4. By an XYZ driving unit 252, the arm unit 202 moves in each of right-and-left (X) direction and back-and-forth (Y) direction relative to an operator, and a tip portion of the arm unit 202 having a laser irradiation exit moves in up-and-down (Z) direction. 206 is a controller having a joystick, a switch and the like for moving the arm unit 202. 209 is a computer unit used to input data necessary for surgery and to perform arithmetic operations of laser irradiation data, which comprises a display monitor 209a, a keyboard 209b used for input and the like.

In FIG. 4, reference numeral 210 is the laser irradiation optical system comprising an excimer laser source 211, a mirror 212, a divided mask 213 constituted from a number of strip-shaped masks arranged side-by-side, a scanning mirror 215, an image rotator 217, an aperture 219 of which aperture diameter is variable, a projecting lens 221, and a dichroic mirror 222 which reflects laser beam but transmits visible light and infrared light. At the time of laser irradiation, each of the strip-shaped mask that the mask 213 has is opened and closed individually so that the laser beam of a thin rectangular shape emitted from the laser source 211 is cut partially in its longitudinal direction. The laser beam having passed through the divided mask 213 is moved by scanning action of the scanning mirror 215 so that selectively limited laser beam is directed onto the cornea Ec.

Reference numeral 230 is the observation optical system comprising an objective lens 231, a dichroic mirror 232 which transmits visible light but reflects infrared light, and a binocular surgical microscope 233. On an optical axis of the objective lens 231, a fixation light 235 is disposed.

Reference numeral 240 is the eye-ball position detecting optical system comprising a lens 241, a mirror 242, an infrared transmission filter 243, and a CCD camera 245 all arranged in a reflecting direction of the dichroic mirror 232. Similarly to the CCD camera 36 included in the corneal topography apparatus 100, the CCD camera 245 is also used for photographing an anterior eye segment for patient's eye identification.

Further, disposed below the dichroic mirror 232 are an illumination light source 246 which emits infrared light, and an illumination light source 247 which emits visible light for adjusting the pupil of the eye E in size upon photographing the anterior eye segment.

Reference numeral 250 is an arithmetic control unit for controlling each unit of the apparatus, and 251 is a frame memory which captures an image outputted from the CCD camera 245. Similarly to the corneal topography apparatus 100, the arithmetic control unit 250 extracts characteristics of the iris pattern of the eye E based on the image of the anterior eye segment photographed by the CCD camera 245 to generate an identification code for identifying the eye E. In addition, the arithmetic control unit 250 detects a position of the eye E relative to the apparatus based on the image of the anterior eye segment photographed by the CCD camera 245 and controls the XYZ driving unit 252 in accordance with the detected result.

Figure 5A:
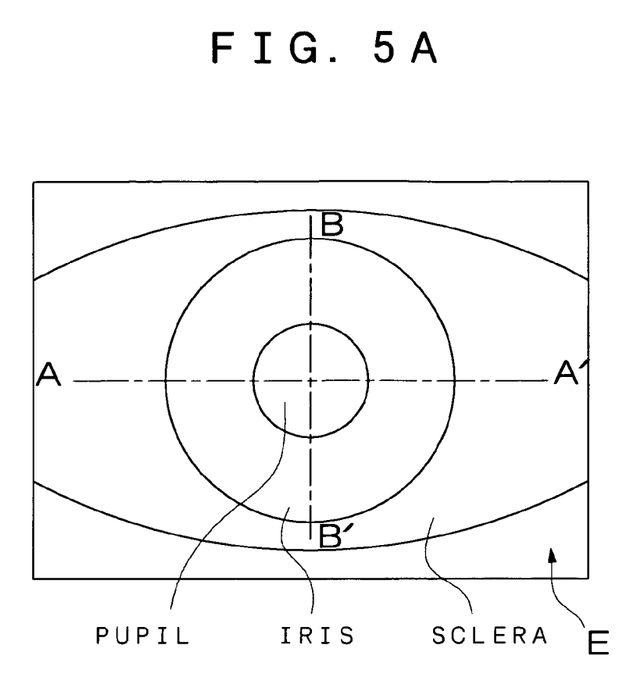
FIGS. 5A and 5B are views illustrating positional detection of a patient eye performed by the corneal surgery apparatus.
Figure 5B:
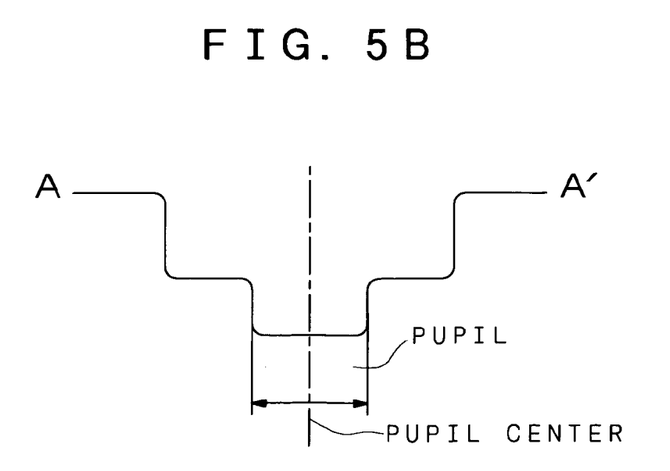

Description is now given to positional detection of the eye E briefly. FIG. 5A is a view showing an image of the anterior eye segment photographed by the CCD camera 245, and FIG. 5B is a view showing distribution of light quantity along the line A–A' of FIG. 5A. As apparent from the figures, the light quantity differs depending on part of the eye, namely pupil, iris and screla. Thus, based on the information on light quantity, coordinates of the pupil edges in a lateral direction can be obtained. Further, by detecting the coordinates of the pupil edges, the center position of the pupil edges, or equivalently coordinates of the pupil center, in a lateral direction can be obtained. In a like manner, coordinates of the pupil center in a vertical direction can be obtained based on information on light quantity along the line B–B'. That is to say, from the both coordinates, it is possible to obtain the position of the pupil center relative to the optical axis of the eye-ball position detecting optical system 245 (or equivalently the optical axis of the laser irradiation optical system 210) which has been brought into a predetermined positional relationship on the photographic element of the CCD camera 245.

For details of the optical systems described above, see U.S. Pat. No. 5,906,608 (Japanese Unexamined Patent Publication No. HEI 9 (1997)-266925), and for details of the eye-ball position detection, see EP 0765648 (Japanese Unexamined Patent Publication Nos. HEI 9 (1997)-149914 and HEI 9 (1997)-192333) and the like.

Figure 6:
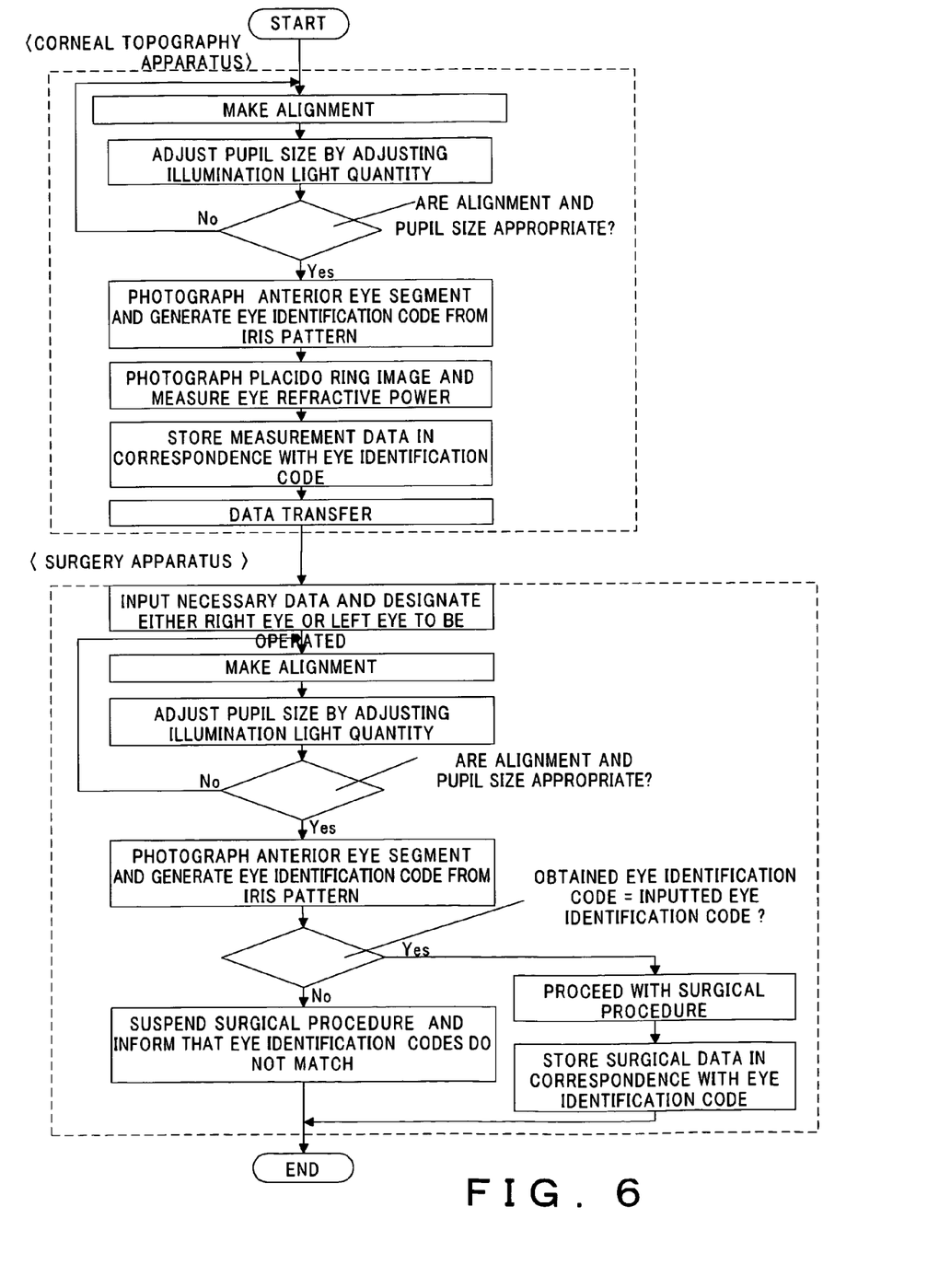
FIG. 6 is a flow chart illustrating operations of the ophthalmic system.

Next, description is given to operations of the both apparatus 100 and 200 referring to the flow chart of FIG. 6. First, operations of the corneal topography apparatus 100 will be explained. While observing the image of the anterior eye segment displayed on the monitor 43, the examiner (here and also in the following description, the term "examiner" and "operator" are intended to be mutually interchangeable) operates the joystick 102 thereby moving the measurement unit 101 relative to a base 103 in order to make rough alignment. Once the image of the target formed on the cornea Ec by the light source 34 comes into a detectable range by the CCD camera 36, the arithmetic control unit 40 obtains coordinates of the target image to detect alignment condition in X and Y directions and drives the XYZ driving unit 47, thereby automatically moving the measurement unit 101 in X and Y directions. The arithmetic control unit 40 also detects alignment condition in Z direction based on signals from the position detecting element 17 and drives the XYZ driving unit 47, thereby automatically moving the measurement unit 101 in Z direction.

After completing alignment, the arithmetic control unit 40 checks whether the image obtained by the CCD camera 36 is suitable for the purpose of extracting characteristics of the eye (the iris pattern). Visible characteristics of the iris changes depending on the pupil size. Therefore, upon capturing an image of the iris pattern, it is required that the arithmetic control unit 40 control light quantity of the illumination light emitted by the light source 30 so as to bring the pupil into a predetermined size. The pupil size can be detected through detection of the pupil edges in the image of the anterior eye segment. In the present preferred embodiment, the light source 30 for eye fixation is used also as an illumination light source for adjusting the pupil size. However, it is also possible to dispose illumination light sources around the optical axis L1 for the dedicated use so that visible light reaches the fundus.

After confirming that alignment has been completed and the pupil size has been optimized, the arithmetic control unit 40 causes the CCD camera 36 to photograph the anterior eye segment automatically. Thereafter, the arithmetic control unit 40 conducts image processing on the image of the anterior eye segment captured in the frame memory 41 to extract characteristics of the eye E thereby generating an identification code which is unique (individual) to the eye E. That is to say, after having obtained the edges of boundary between the pupil and the iris, coordinates representing light and dark in the iris pattern are digitized to obtain the identification code (to generate the identification code).

Consequently, photographing for analyzing corneal shape and eye refractive power measurement are carried out. Since the apparatus has been already aligned with the eye E, photographing of the placido ring image can be started immediately. The arithmetic control unit 40 turns on the light sources 3 for a predetermined period of time to form an image of the placido ring on the cornea Ec. The image of the placido ring formed on the cornea Ec is photographed by the CCD camera 36 and captured into the frame memory 41. The arithmetic control unit 40 conducts predetermined image processing on the image to carry out the edge processing of the image of the placido ring, to obtain distribution of corneal curvatures at each predetermined angle step, and to obtain data on the corneal shape (corneal topography data). Thereafter, the arithmetic control unit 40 performs measurement using the eye refractive power measurement optical system 20 to obtain data on the distribution of the eye refractive powers, and then stores these measurement data in the memory 46 in association with ((paired with/assigning) hereinafter referred to simply as "in association with") the identification code described above.

In a like manner, measurement of the other eye is carried out. Characteristics of the eye (the iris pattern) differ between the right eye and the left eye of the same individual. Therefore, in this case too, the arithmetic control unit 40 obtains an identification code through photographing an image of the anterior eye segment, and then stores the measurement data into the memory 46 in association with the identification code.

Here, in case where it takes long to conduct image processing on the iris pattern and the image of the placido ring, each image is once stored into another memory and analyzed later. In addition, it is possible to perform photographing of the anterior eye segment to obtain its iris pattern after photographing for corneal topography or eye refractive power measurement is performed. In this case too, the photographing is carried out as a part of a measurement routine after alignment for measurement has been made. That is to say, an image for eye identification is obtained without the patient being aware of it so that the examiner can carry out the photographing effectively without much trouble.

Once measurement data on both eyes are obtained, by operating switches of the switch unit 49, the data are transferred from an output unit 48 of the corneal topography apparatus 100 to an input unit of the corneal surgery apparatus 200 (an input unit of the computer 209). The data may be transferred (inputted and outputted, hereinafter referred to simply as "transfer") using cable communications, floppy disks or the like. At this time, the measurement data on right eye and left eye are transferred in association with the respective identification codes.

Next, description is given to operations of the corneal surgery apparatus 200. The computer 209 receives input of the measurement data obtained by the corneal topography apparatus 100 as well as data necessary for surgery such as post-correction refractive power, optical zone and the like. In addition, whether the eye E is the left eye or the right eye is designated using the key board 209b. From the inputted data, the computer 209 calculates laser irradiation data such as ablation amount of cornea and the like. The calculated laser irradiation data are transferred to the arithmetic control unit 250 with the same identification code that is originally assigned to the measurement data from which the laser irradiation data are calculated. (Here, it is possible to calculate and transfer laser irradiation data only on the designated side of the eye, or to calculate laser irradiation data on both eyes and transfer the laser irradiation data only on the designated side of the eye.)

The operator makes the patient lie down on a bed, and positions the arm portion 202 having the laser irradiation exit above the designated eye E while observing the eye E using the surgical microscope 233. If the pupil center is in a detectable range by the eye-ball position detecting optical system 240, the arithmetic control unit 250 controls drive of the XYZ driving unit 252 thereby moving the arm unit 202 so as to make alignment with the eye E. Further, the arithmetic control unit 250 controls the light source 247 to adjust illumination light quantity thereof so that the pupil of the eye E is brought into a predetermined size.

After confirming that alignment has been completed and the pupil size has been optimized, the arithmetic control unit 250 causes the CCD camera 245 to photograph the anterior eye segment automatically. Thereafter, similarly to the case of the corneal topography apparatus 100, the arithmetic control unit 250 conducts predetermined image processing on the image of the anterior eye segment captured in the frame memory 251 to extract characteristics of the eye E, thereby obtaining an identification code which is unique (individual) to the eye E. Then, the newly-obtained identification code and the identification code that is inputted with the measurement data (that is assigned to the laser irradiation data) are compared to see if they match. If they match, the arithmetic control unit 250 gives permission to perform the reminder of the operation process. When the operator inputs signals to trigger laser irradiation using a foot switch 208, the arithmetic control unit 250 emits laser beam from the laser source 211 and irradiates the cornea Ec with the laser beam based on the laser irradiation data. During the laser irradiation, eye tracking is performed automatically based on the result of detection by the eye-ball position detecting optical system 240. Further, the surgery data (the inputted data necessary for surgery, the obtained laser irradiation data and the like) are stored in the computer 209 in association with the identification code.

On the other hand, if the identification codes do not match, the arithmetic control unit 250 suspends (restricts) the reminder of the operation process to be carried out. In that case, the arithmetic control unit 250 displays a message informing the situation on the monitor 209a, and generates a warning sound from a sound generating unit 253. In this manner, the arithmetic control unit 250 informs the operator that the eye E and the inputted measurement data (the laser irradiation data obtained based on the measurement data) do not correspond. When performing surgery, it is undoubtfully necessary to confirm that the inputted measurement data are the data on the patient himself. In addition, even if the data are certainly of the patient himself, it is also important to ensure not to mistake the data on right or left eye for the other. Here, as described above, by comparing the identification code that is obtained immediately before the surgery with the identification code corresponding the measurement data and the like, it is strictly checked if the data for right or left eye are mistaken for the other. As the result, the surgery is prevented from proceeding further when the data are inconsistent.

The corneal surgery apparatus 200 herein is provided with means for photographing the anterior eye segment (the CCD camera 245 in this preferred embodiment) in order to generate identification codes based on the iris pattern. In an alternative embodiment, an identification code generator may be provided in a vicinity of the apparatus for the dedicated use.

Up to this point, description has been given to the example in which the measurement data obtained by the corneal topography apparatus 100 are transferred directly to the corneal surgery apparatus 200. Hereinafter, description is given to an example in which each measurement data obtained by a plurality of ophthalmic apparatus are managed collectively in a form of a database with reference to FIG. 7.

Figure 7:
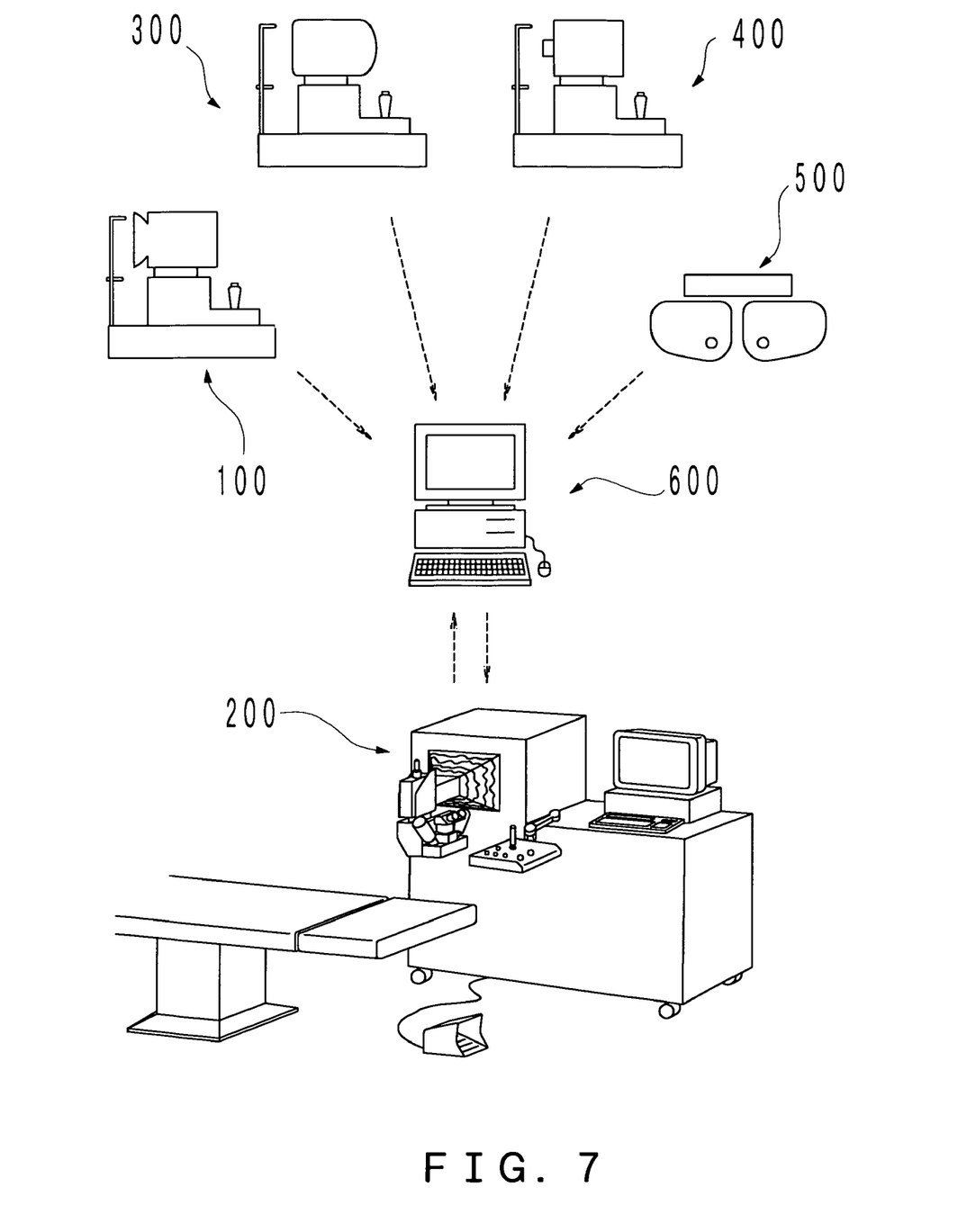
FIG. 7 is a view illustrating an example of integral data management of measurement data obtained by a plurality of ophthalmic apparatus.

In FIG. 7, reference numeral 600 is a computer used for data management, and a database having a data management program is installed therein. Besides the measurement data obtained by the corneal topography apparatus 100 described above, the computer 600 receives data transferred thereto including measurement data obtained by a noncontact tonometer 300, a fundus camera 400, a subjective optometry apparatus 500 and the like as well as the surgery data obtained by the corneal surgery apparatus 200.

Figure 8:
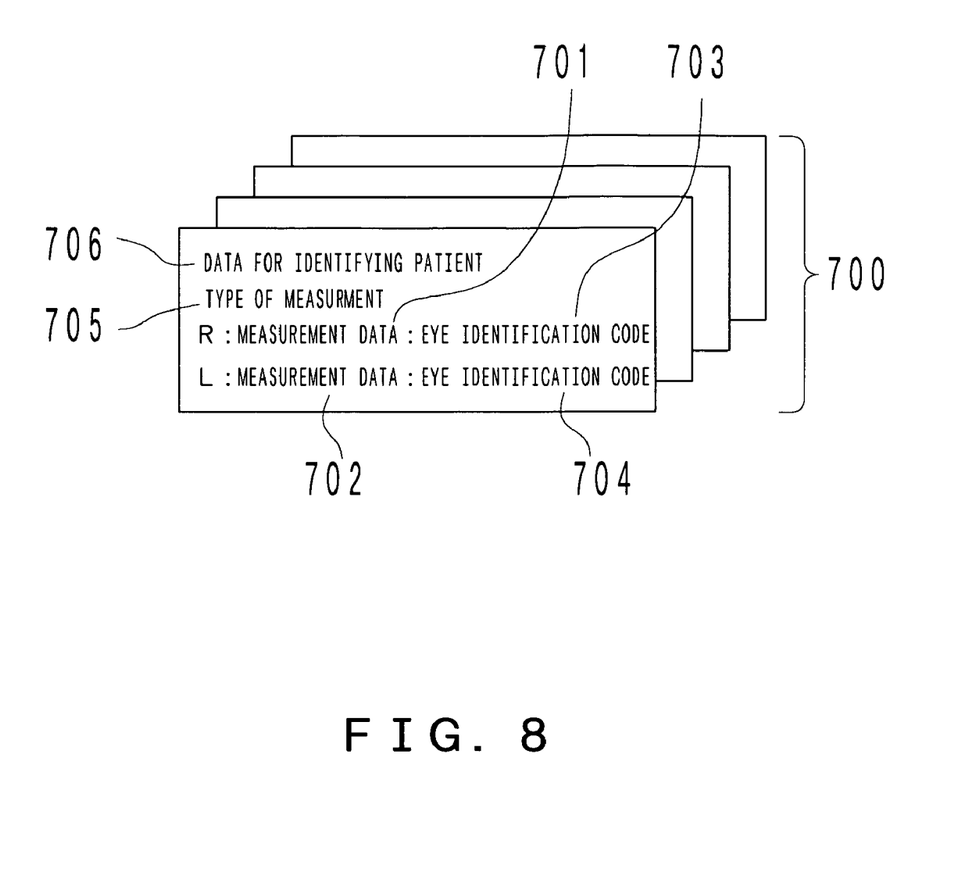
FIG. 8 is a view showing an example of a data file obtained by an ophthalmic apparatus.

For example, a data file 700 obtained by the corneal topography apparatus 100 as described above includes the measurement data for right eye 701 and for left eye 702; the identification codes 703 and 704 which correspond the respective measurement data 701 and 702 in association with each other. Besides, the data file 700 also includes data 705 indicating a type of measurement, data 706 for patient identification such as an identification number, a name or the like (see FIG. 8). This data file 700 is transferred to the computer 600. The data 706 for patient identification do not necessarily have to be transferred simultaneously, instead they may be inputted at the side of the computer 600.

The noncontact tonometer 300 and the fundus camera 400 comprise photographing means for observing the anterior eye segment. In the case of these ophthalmic apparatus also, an identification code is generated separately for each eye of the same individual similarly to the case of the corneal topography apparatus 100, and the data file 700 including the measurement data and the identification code assigned to the data is transferred to the computer 600. Measurement data obtained by the subjective optometry apparatus 500 do not have identification codes assigned thereto so that the measurement data in this case are managed by the data 706 for patient identification. The computer 600 manages the measurement data, which are transferred from each ophthalmic apparatus, separately for each patient based on the data 706 for patient identification, and further manages the data on each patient separately for each eye based on the identification codes 703 and 704.

Here, the identification codes are generated by encoding the iris pattern so that large storage capacity is required. Therefore, if all the identification codes are stored in association with the measurement data transferred from each apparatus, the storage capacity required to meed this end is inevitably increased. To avoid this, the computer 600 manages the transferred data in the following way (see FIG. 9).

Figure 9:
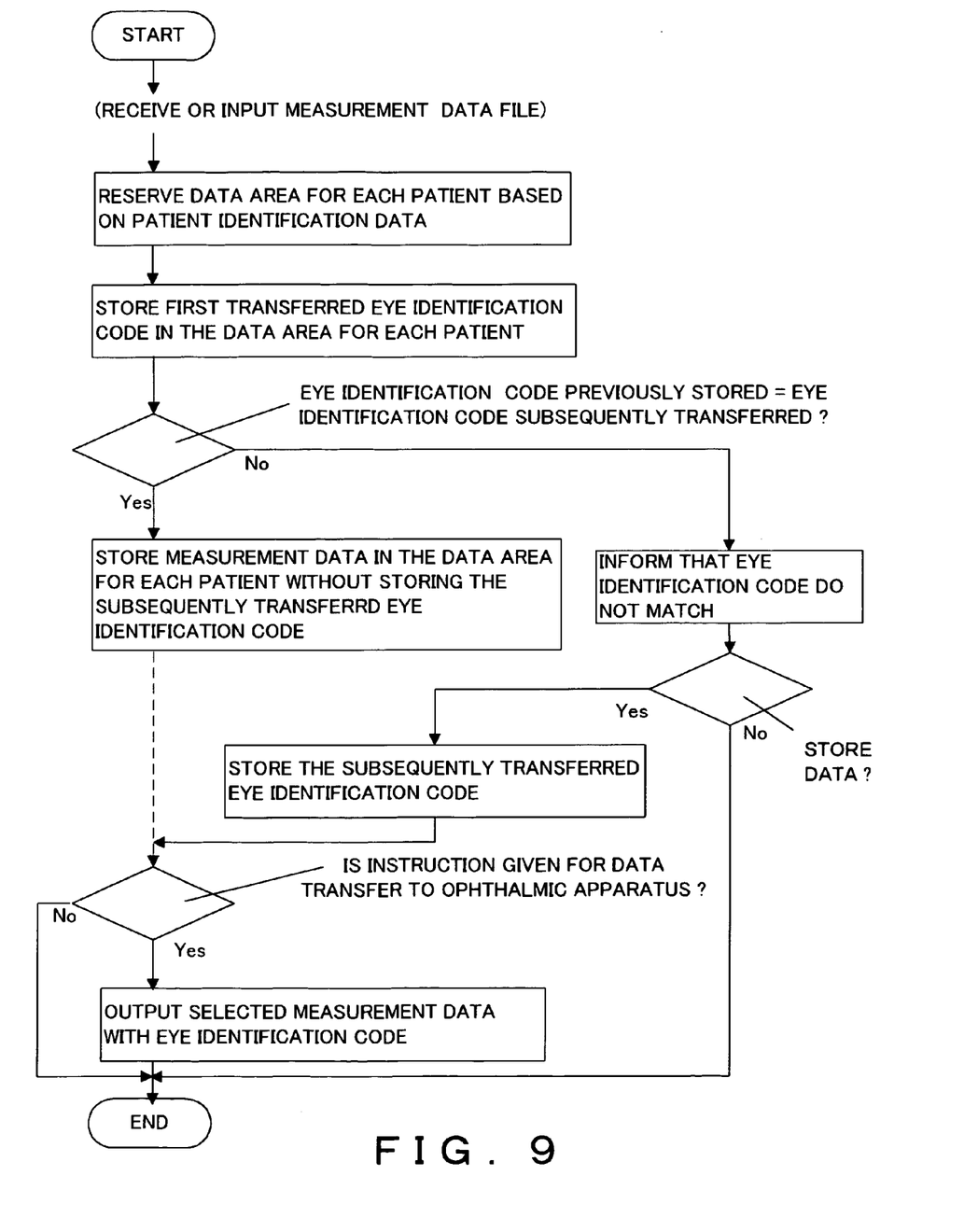
FIG. 9 is a flow chart illustrating data management by a computer.

First, a data area is reserved for each patient based on the data 706 for patient identification, and the measurement data transferred from each apparatus are stored in association with the data 706 for patient identification. Here, the identification code that has been transferred first is stored. In the case where a plurality of measurement data are transferred from a plurality of ophthalmic apparatus together with the identification codes, the identification code that has been stored first and the identification code that is transferred later are compared (checked) with each other. If the two identification codes are the same, the identification code that is transferred later is discarded to avoid storing the same identification codes in duplication (to integrate into at least one identification code). This reduces spending of the storage capacity even in the case of storing the measurement data together with the identification codes.

As the result of checking the identification codes, if they do not match, the situation is displayed on a monitor or the like as warning. In response to this warning, confirmation is made to see whether the data 706 for patient identification, such as an identification number or a name, correctly correspond to the measurement data (whether there is an input error of the data for patient identification) and necessary step is taken to deal with the situation. After such confirmation, there may be the case where instructions to store the data are given. In that case, the computer 600 stores the measurement data and the identification code in association with each other. As described above, in the case of managing the each measurement data based on ID numbers or names, provided that identification codes are assigned to the data, the data management is carried out more strictly. Needless to say, this applies to the case, for example, where measurement data on one and the same patient is transferred from one ophthalmic apparatus at different time, or from a plurality of ophthalmic apparatus.

In the case where instructions are given so as to selectively transfer necessary data to other ophthalmic apparatus, such as the corneal surgery apparatus 200, the computer 600 transfers selected measurement data with the identification codes. Upon data transfer, even in the case of the data which identification codes are not assigned at the time of input such as the data inputted from the subjective optometry apparatus 500, identification codes are assigned to such data. At the side of the corneal surgery apparatus 200, the identification code obtained by photographing the eye to be operated in the above manner is compared with the identification code assigned to the measurement data to see if they match. As the result, the measurement data used for the eye to be operated can be strictly checked.

In the preferred embodiment described above, the iris patterns are used for eye identification. Yet, retinal vasculature patterns of the eyes also have excellent characteristics for eye identification. Accordingly, it is highly applicable to obtain the identification codes from the retinal vasculature patterns upon measurement or surgery. In this case too, photographing means included in the ophthalmic apparatus can be used both for eye identification and for observation of the eye or the like.

As described above, according to the present invention, measurement data are managed in association with patients' eyes (patients) by strict (highly reliable) identification codes.

Further, in the case of ophthalmic surgery apparatus which uses measurement data obtained by another ophthalmic apparatus, it is ensured that the measurement data and a patient's eye to be operated match.

Still further, in the case of managing measurement data obtained by a plurality of ophthalmic apparatus, the measurement data are managed separately for each patient's eye (patient) even more accurately, and the storage capacity required thereby can be reduced.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic surgery system comprising an ophthalmic measurement apparatus and a refractive correction surgery apparatus, wherein the ophthalmic measurement apparatus comprises:

optometry means having a measurement optical system for measuring a patient's eye to obtain measurement data on the eye necessary for refractive correction;

first alignment means for aligning an optical axis of the measurement optical system with a predetermined position of the eye;

first photographing means for photographing an anterior segment of the eye under a condition that the optical axis of the measurement optical system is aligned with the predetermined position of the eye by the first alignment means;

first identification code acquiring means for extracting an iris pattern, which is inherently unique to the eye, by processing a first image of the eye anterior segment photographed by the first photographing means during the measurement of the eye, and obtaining a first identification code based on the extracted iris pattern;

storage means for storing the obtained measurement data or surgical data on the eye for the refractive correction generated based on the obtained measurement data in association with the obtained first identification code, and output means for outputting the measurement data or the surgical data along with the associated first identification code which are stored in the storage means, and the refractive correction surgery apparatus comprises:

surgery means for performing surgery for the refractive correction on the eye by irradiating a cornea of the eye with a laser beam for ablation, the surgery means having an irradiation optical system for irradiating the laser beam onto the cornea;

second alignment means for aligning an optical axis of the irradiation optical system with a predetermined position of the eye;

second photographing means for photographing the eye anterior segment under a condition that the optical axis of the irradiation optical system is aligned with the predetermined position of the eye by the second alignment means;

second identification code acquiring means for extracting the iris pattern by processing a second image of the eye anterior segment photographed by the second photographing means before the irradiation of the laser beam, and obtaining a second identification code based on the extracted iris pattern;

comparison means for comparing the first identification code received from the ophthalmic measurement apparatus and the obtained second identification code to judge whether the first identification code and the second identification code match; and permission means for permitting the surgery to be performed by the surgery means based on the surgical data received from the ophthalmic measurement apparatus, or permitting the surgical data to be generated based on the measurement data received from the ophthalmic measurement apparatus when the comparison means judges that the first identification code and the second identification code match.

2. An ophthalmic system comprising an eye examination apparatus and a data management apparatus:

wherein the eye examination apparatus comprises:

optometry means for measuring a patient's eye to obtain measurement data on the eye necessary for refractive correction;

photographing means for photographing an anterior segment of the eye;

first identification code acquiring means for extracting an iris pattern, which is inherently unique to the eye, by processing a first image of the eye anterior segment photographed by the photographing means during the measurement of the eye, and obtaining a first identification code based on the extracted iris pattern;

first storage means for storing the obtained measurement data or surgical data for the refractive correction generated based on the obtained measurement data in association with the obtained first identification code; and first output means for outputting the measurement data or the surgical data along with the associated first identification code which are stored in the first storage means; wherein the data management apparatus comprises:

input means for inputting a second image of the eye anterior segment;

second identification code acquiring means for extracting the iris pattern by processing the input second image, and obtaining a second identification code based on the extracted iris pattern;

associating means for associating the obtained second identification code with a data storage area;

comparison means for comparing the first identification code received from the eye examination apparatus and the second identification code to judge whether the first identification code and the second identification code match; and second storage means for storing the measurement data or the surgical data in association with the first identification code received from the eye examination apparatus in the data storage area in association with the second identification code when the comparison means judges that the first identification code and the second identification code match; and second output means for outputting the measurement data or the surgical data along with the associated second identification code which are stored in the second storage means to a refractive correction surgery apparatus for the refractive correction.

3. An ophthalmic system comprising an eye examination apparatus and a data management apparatus, wherein the eye examination apparatus comprises:

optometry means for measuring a patient's eye to obtain measurement data on the eye necessary for refractive correction;

photographing means for photographing an anterior segment of the eye;

identification code acquiring means for extracting an iris pattern, which is inherently unique to the eye, by processing an image of the eye anterior segment photographed by the photographing means during the measurement of the eye, and obtaining an identification code based on the extracted iris pattern;

first storage means for storing the obtained measurement data or surgical data for the refractive correction generated based on the obtained measurement data in association with the obtained identification code; and first output means for outputting the measurement data or the surgical data along with the associated identification code which are stored in the first storage means, and the data management apparatus comprises:

second storage means for storing the measurement data or the surgical data along with the associated identification code which are received from the eye examination apparatus into a data storage area and associating the identification code with the data storage area;

comparison means for comparing the identification code stored in the second storage means and the identification code newly received from the eye examination apparatus to judge whether the stored identification code and the newly received identification code match;

assigning means for assigning the measurement data or the surgical data newly received from the eye examination apparatus in the data storage area in association with the identification code when the comparison means judges that the stored identification code and the newly received identification code match; and second output means for outputting the measurement data or the surgical data along with the identification code which are stored in the second storage means to a refractive correction surgery apparatus for the refractive correction.

* * * * *